United States Patent [19]

Carswell, Jr.

[11] Patent Number: 5,192,270

[45] Date of Patent: Mar. 9, 1993

[54] HYPODERMIC SYRINGE AND A METHOD FOR MARKING INJECTIONS

[76] Inventor: Donald D. Carswell, Jr., 3100 Merritt Pkwy., Reading, Pa. 19609

[21] Appl. No.: 615,325

[22] Filed: Nov. 19, 1990

[51] Int. Cl.⁵ .............................................. A61M 5/00
[52] U.S. Cl. ................................. 604/116; 604/192; 604/187; 604/218; 606/116
[58] Field of Search ............... 604/116, 112, 187, 218, 604/192, 46, 110, 194; 606/116, 117

[56] References Cited

U.S. PATENT DOCUMENTS

| | | | |
|---|---|---|---|
| 3,039,467 | 6/1962 | Stone et al. | 606/116 |
| 3,470,011 | 9/1969 | Szumski et al. | 604/46 |
| 3,999,504 | 12/1976 | Kearse | 604/116 |
| 4,243,035 | 1/1981 | Barrett | 604/218 |
| 4,349,338 | 9/1982 | Heppler | 40/594 |
| 4,392,493 | 7/1983 | Niemeijer | 606/116 |
| 4,636,201 | 1/1987 | Ambrose et al. | 604/192 |
| 4,799,926 | 1/1989 | Haber | 604/187 |
| 4,838,854 | 6/1989 | Kuzmanovich | 604/116 |
| 4,862,772 | 9/1989 | Piperato | 604/110 |

Primary Examiner—C. Fred Rosenbaum
Assistant Examiner—Chalin Smith

[57] ABSTRACT

A hypodermic syringe is provided with a colorant disposed at a readily accessible portion of the syringe so that when the colorant is touched against the skin of a patient, the colorant is transferred to the skin of the patient giving a visual indication of the point at which an injection has or will be given. The plunger of the hypodermic syringe is provided with an axially disposed receptacle adapted to receive and retain the needle of the syringe.

9 Claims, 1 Drawing Sheet

HYPODERMIC SYRINGE AND A METHOD FOR MARKING INJECTIONS

BACKGROUND OF THE INVENTION

1. Field of the Invention

This invention relates to an improved hypodermic syringe and a method for its use that facilitates marking the points on a human body where injections have been or are to be given. Another aspect of the invention is an integrally contained means for safely detaching and disposing of used syringe needles.

2. Description of the Prior Art

Hypodermic syringes are used, as is well known, to inject liquid mendicants into the body for a variety of medical reasons. In some cases a person is given an injection only at widely scattered intervals, such as a tetanus shot after suffering a puncture wound. In other instances, though, some people need repeated injections on a regular day-to-day basis. Illustrative of this type of medical treatment is found with a diabetic person who may be required to receive an injection of insulin on a daily or even more frequent basis. So too, repetitive preventative injections may be given for flue, allergies tetanus and the like.

Each time the skin is punctured with a hypodermic needle, the skin and underlying flesh are cut and traumatized, albeit to a minor degree. But unless a healing period such as a month or so is permitted, repeated injections made at the same spot on the body may become painfully sore and, in the extreme, a callus of hardened matter may form over the skin or hard lumps may develop under the skin.

To allow for the healing process, it is considered good practice to select a new location of injection with every injection. Sometimes, to help new patients, they are asked to imagine a matrix of intersecting horizontal and vertical lines on their skin separated by a quarter of an inch or so. The points of intersection will suggest successive injection points properly spaced from each other. When this is done, a careful patient may successively work his way through the intersections of the matrix and avoid giving himself repeated injections at the same locations. However, unless indelible intersecting lines are actually drawn on the skin, which is seldom the case, the success of this method in avoiding repeated injections at the same point is subject to the vagaries of the recollection of the patient.

It is a rule of thumb that one should not give an injection at the same spot more than once a month. If done more frequently, necrosis of tissue may occur as well the formation of an abscess. One consequence of these injuries that is of concern to the diabetic, is that the absorption of insulin can be retarded and the dosage may need to be increased to achieve desired results. This presents a potential danger as a lesser dose may be required at other locations which have normal absorption to avoid giving an overdose with potentially serious reactions.

While not of serious medical concern, repeated injections in the same area can lead to the development of atrophies of the subcutaneous fat which are cosmetically displeasing.

It is also known that a problem may be associated with the disposal of used needles. Much publicity has recently been given to hospital wastes that have washed up on beaches, including used syringes with exposed needles. If a bather steps on a needle or otherwise makes contact with it, he may suffer a puncture wound that could present a danger of serious infections.

SUMMARY OF THE INVENTION

Accordingly, it is an object of this invention to provide a simple method for marking the spot at which an injection has been or will be given.

Another object of this invention is to provide a hypodermic syringe that is adapted to permit the user to mark the spot at which an injection was or will be given.

Another object of the invention is to provide an integrally contained means associated with the hypodermic syringe to provide for the detachment and the safe disposal of used needles.

These and other objects of this invention are achieved by utilizing the end of the removable cover which protects the needle of a syringe, to mark an injection site. This is accomplished by placing a small amount of coloring material on the end of the needle protective cover so that the colorant, when dry or wetted and touched against the skin, will provide a visible indication of the injection site.

Additionally, it is within the scope of the invention to provide an axially extending receptacle in the plunger of the hypodermic syringe that is adapted to receive a needle for detachment and safe disposal.

While the discussion of this invention as it relates to marking injection sites is primarily directed to the patient who gives himself injections, it can easily be appreciated that the problem of avoiding repeated injections at the same point may be even more acute with respect to nurses and doctors who scarcely can be expected to remember the last injection site or an imaginary matrix of lines from patient to patient from day to day.

DESCRIPTION OF THE DRAWINGS

The invention may better be understood from the following description of the drawings in which.

DETAILED DESCRIPTION OF THE DRAWINGS

Figure 1:
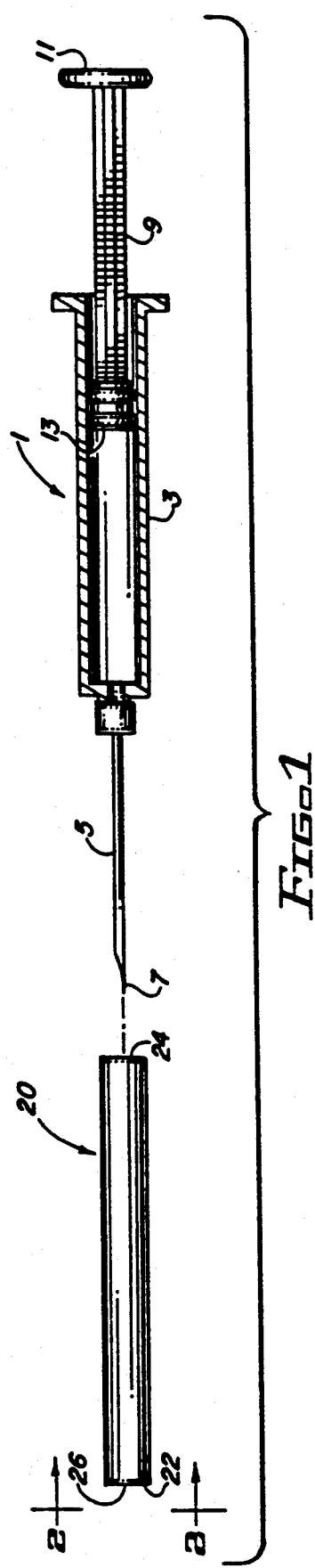
FIG. 1 is a side view of a hypodermic syringe and its protective cover which form the basis of the invention.
Figure 2:
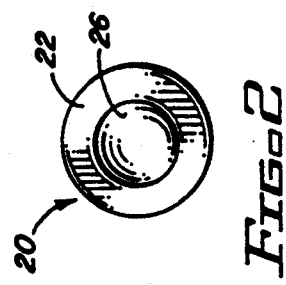
FIG. 2 is an end view of the closed end of the protective cover taken along line 2—2 of FIG. 1.

In FIG. 1 there is shown a syringe 1 having a cylindrical body portion 3. A hollow needle 5 is attached at one end of the syringe 1 in sealed fluid communication with the cylinder 3. The exposed end of the needle 5 carries a sharpened end 7 suitable for insertion under the skin.

A plunger 9 is provided to slide back and forth within the cylinder 3. The outer exposed end of the plunger 9 carries an enlarged portion which serves as a thumb rest 11. The inner end of the plunger 9 carries a piston head 13.

Associated with the syringe 1 is a removable protective cover 20 for the needle 5. One end of the protective cover 20 has an open end 24 adapted to receive the needle 5 while the opposite end of the protective cover 22 is closed. In the preferred embodiment of this invention the closed end 22 of the protective cover 20 has a small indented dimple 26.

In the practice of the invention a small amount of a pigment, dye or other coloring material is deposited within the dimple 26. The coloring material is selected so that it will leave a visible mark when the free end 22 of the protective cover 20 is touched against the skin. The coloring material may transfer a mark in the dry condition or it may be selected to be water or alcohol soluble. In this latter regard, brief contact of the coloring material with tap water or alcohol from a swab, used to cleanse the skin prior to injection, will render selected dry colorants fluent and facilitate the application of a good, clear mark with minimum time, pressure and effort. In the preferred practice of this invention, the dimple 26 is pressed against the skin immediately following an injection to provide a mark that is of sufficient intensity and durability to be recognizable when the user is given his next injection. The mark may also be made on the skin prior to the injection, but this may cause the colorant to be carried under the skin an leave a "tattoo".

From the foregoing it can be understood that through the practice of this invention, it is easy for a patient, nurse or doctor to work his way up or down or from side to side from the point of the previous injections following a visualized matrix of intersecting lines. By providing a handy apparatus as an integral part of the syringe to mark the skin when an injection is given, it becomes a simple matter to keep account of the point at which the last injection was given and so avoid making repeated injections at the same point.

It is to be understood that the invention consists of affixing a small amount of a dye or other coloring material to a hypodermic syringe in a location that makes it convenient to press the syringe against the skin, when dry or wetted depending on the nature of the coloring material, and transfer the coloring material to the skin. As such, the location of the dye or coloring material on the syringe is not critical, but may be placed at any convenient location. For example, in addition to locating the dye or coloring material at the closed end of the protective cover, it could also be located on the rim of the open end of the protective cover. So too, dye or coloring material could be located on the thumb rest or any other convenient location on the syringe. Thus, while in the preferred practice of this invention the dye or coloring material is placed on a dimple on the closed end of the protective cover, it is not intended that the invention be so limited.

The selection of the coloring material that is placed in the dimple 26 is not critical to the practice of this invention provided only that the coloring material has the ability to transfer a clearly visible mark to the skin and that the coloring material has sufficient permanency to survive until the next injection is given. As examples of suitable and convenient coloring materials there may be mentioned iodine, mercurochrome or methiolate, food colorings and the like, any of which, after they have been wetted by a solvent liquid, such as water or alcohol as may be appropriate, will, upon contact, mark the skin with a dark, clearly observable indicia that will persist until it is time for the next injection to be given, even though it be several days later.

In a further embodiment of this invention, the plunger 9, as best can be seen in FIG. 3, is provided with an axially disposed hollow receptacle 10. The receptacle 10 is designed to accept the needle 5. Then, after an injection has been given, the plunger 9 is removed from the cylinder 3 and the needle 5 is inserted into the receptacle 10 in the plunger 9 and the cylinder 3 is rocked back and forth a few times until the needle breaks loose from the cylinder body 3 and is so embedded in the interior of the plunger 9. This procedure performs two very useful functions. First, it renders the syringe inoperative so that it will not intentionally or inadvertently be used again and, second, it removes much of the hazard of disposing of the syringe since the sharp needle is protectively encapsulated within the body of the plunger 9.

I claim:

1. A hypodermic syringe including a cylindrical body portion, a needle attached in sealed fluid communication with the body portion and a removable protective cover for the needle which cover is closed at one end and open at the other end to receive the needle, characterized in that a colorant is disposed on one end of the cover, said colorant adapted to print a visible indicia when the one end is pressed against the skin.

2. A hypodermic syringe according to claim 1 wherein a dimple is provided at the closed end of the needle protective cover and the colorant is disposed within the dimple.

3. A hypodermic syringe according to claim 1 wherein the colorant is rendered fluent by contact with a liquid.

4. A hypodermic syringe according to claim 3 wherein the colorant is water soluble.

5. A hypodermic syringe according to claim 4 wherein the colorant is a food coloring.

6. A hypodermic syringe according to claim 3 wherein the colorant is alcohol soluble.

7. A hypodermic syringe according to claim 6 wherein the colorant is mercurochrome, methiolate or iodine.

8. A method for marking the spot on the human skin where an injection has been given with a hypodermic syringe which syringe includes a cylindrical body portion, a needle attached in sealed fluid communication with the body portion and a removable protective cover for the needle, comprising the steps of:
    depositing a small amount of a colorant on one end of the removable protective cover and
    contacting the skin with the one end of the protective cover to transfer colorant to the skin.

9. A method according to claim 8 including the step of rendering the colorant fluent before contacting the skin by contacting the colorant with a solvent for the colorant.

* * * * *